(12) United States Patent
Southerland et al.

(10) Patent No.: US 10,846,370 B2
(45) Date of Patent: Nov. 24, 2020

(54) TECHNIQUES FACILITATING MOBILE TELEMEDICINE FOR STROKE PATIENTS

(71) Applicant: University of Virginia Patent Foundation, Charlottesville, VA (US)

(72) Inventors: Andrew M. Southerland, Charlottesville, VA (US); Sherita N. Chapman Smith, Charlottesville, VA (US); Brian S. Gunnell, Scottsville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1254 days.

(21) Appl. No.: 14/910,890

(22) PCT Filed: Aug. 19, 2014

(86) PCT No.: PCT/US2014/051664
§ 371 (c)(1),
(2) Date: Feb. 8, 2016

(87) PCT Pub. No.: WO2015/026808
PCT Pub. Date: Feb. 26, 2015

(65) Prior Publication Data
US 2016/0188829 A1    Jun. 30, 2016

Related U.S. Application Data

(60) Provisional application No. 61/867,477, filed on Aug. 19, 2013.

(51) Int. Cl.
*G16H 40/40* (2018.01)
*G06F 19/00* (2018.01)
(Continued)

(52) U.S. Cl.
CPC ......... *G06F 19/3418* (2013.01); *G06Q 10/10* (2013.01); *G06Q 50/22* (2013.01);
(Continued)

(58) Field of Classification Search
CPC .. G06F 19/3418; G06F 19/321; G06F 19/325; G16H 80/00; G16H 10/60;
(Continued)

(56) References Cited

U.S. PATENT DOCUMENTS

| 6,058,370 A | 5/2000 | Church et al. |
| 2005/0038326 A1 | 2/2005 | Mathur |

(Continued)

FOREIGN PATENT DOCUMENTS

WO    WO-2015026808 A1    2/2015

OTHER PUBLICATIONS

"TeleBAT: Mobile Telemedicine for the Brain AttackTeam", LaMonte, et al., Journal of Stroke and Cerebrovascular Diseases, vol. 9, No. 3 (May-Jun. 2000): pp. 128-135 (Year: 2000).*

(Continued)

*Primary Examiner* — Joseph D Burgess
(74) *Attorney, Agent, or Firm* — Schwegman Lundberg & Woessner, P.A.

(57) ABSTRACT

A method for facilitating mobile telemedicine for a suspected stroke case can include initiating, with an evaluation device, a prehospital mobile telemedicine videoconference with a remote device when a projected amount of time exceeds a threshold. The method can include determining for presentation, a set of specified symptoms of a stroke, the specified symptoms obtained remotely using the prehospital mobile telemedicine videoconference, obtaining input from a user, including information indicative as to whether a patient is exhibiting symptoms of a stroke, and in response to obtaining input, transmitting, from the evaluation device (Continued)

to the remote device, the information indicative as to whether the patient is exhibiting symptoms of a stroke. The method can include generating a medical alert, at the evaluation device, the medical alert including patient information and the information indicative as to whether the patient is exhibiting symptoms of a stroke.

25 Claims, 3 Drawing Sheets

(51) Int. Cl.
*G16H 80/00* (2018.01)
*G06Q 10/10* (2012.01)
*G06Q 50/22* (2018.01)
*H04N 7/14* (2006.01)
*H04N 7/15* (2006.01)

(52) U.S. Cl.
CPC ............. *G16H 80/00* (2018.01); *H04N 7/142* (2013.01); *H04N 7/15* (2013.01)

(58) Field of Classification Search
CPC ........ G16H 40/20; G16H 40/63; G16H 50/20; G16H 40/67; G16H 20/00; G16H 20/10; G16H 30/20; G16H 50/30; G06Q 50/22
See application file for complete search history.

(56) References Cited

U.S. PATENT DOCUMENTS

| | | | |
|---|---|---|---|
| 2009/0292555 A1 | 11/2009 | Brown | |
| 2011/0047406 A1* | 2/2011 | Smith | H04L 51/30 714/4.12 |
| 2012/0197665 A1* | 8/2012 | Lewis | G06F 19/3481 705/3 |
| 2013/0096649 A1* | 4/2013 | Martin | G06F 19/3418 607/60 |

OTHER PUBLICATIONS

"Target Stroke Manual", American Stroke Association, Feb. 20, 2010 (Year: 2010).*
"International Application Serial No. PCT/US2014/051664, International Search Report dated Dec. 18, 2014", 2 pgs.
"International Application Serial No. PCT/US2014/051664, Written Opinion dated Dec. 18, 2014", 7 pgs.
"Using Tablets, Telemedicine to Speed Stroke Treatment", UVA Today, [Online]. Retrieved from the Internet: <URL: https://news.virginia.edu/content/using-tablets-telemedicine-speed-stroke-treatment, (Jan. 6, 2014), 2 pgs.
Bergrath, Sebastian, et al., "Feasibility of Prehospital Teleconsultation in Acute Stroke—A Pilot Study in Clinical Routine", PLOS ONE., [Online]. Retrieved from the Internet: <http://www.plosone.org/article/fetchObject.action?uri=info%3Adoi%2F10.1371%2Fjournal.pone.0036796&representation=PDF>, (May 18, 2012).

* cited by examiner

TECHNIQUES FACILITATING MOBILE TELEMEDICINE FOR STROKE PATIENTS

CLAIM OF PRIORITY

This application is a U.S. National Stage Filing under 35 U.S.C. § 371 from International Application No. PCT/US2014/051664, entitled "Techniques Facilitating Mobile Telemedicine for Stroke Patients," filed on Aug. 19, 2014, and published as WO 2015/026808 on Feb. 26, 2015, which claims the benefit of priority of U.S. Provisional Patent Application Ser. No. 61/867,477, entitled "Method, System and Computer Readable Medium for Improving Treatment Times for Rapid Evaluation of Acute Stroke via Mobile Telemedicine," filed on Aug. 19, 2013, the content of which are hereby incorporated by reference herein in their entirety.

BACKGROUND

Stroke is a leading cause of long-term disability and death in the United States. In patients suffering from an ischemic stroke, delayed treatment is extremely serious. One effective treatment for ischemic stroke is treatment with thrombolysis. Due to the nature of a stroke, any delay in the time it takes to accurately diagnose a patient and implement treatment can be devastating to the patient. Put another way, diagnosis and treatment techniques that cause unnecessary delay are undesirable. Currently, patients suspected to have symptoms of a stroke are treated quickly once they arrive at a hospital. However, time a patient spends in an ambulance is often wasted as only limited treatment or diagnostic activity is possible. A number of approaches have been made to utilize ambulance time in treatment or diagnosis of a potential stroke victim, but each of these approaches has suffered from low accuracy of stroke recognition or high costs, especially for rural areas.

OVERVIEW

As mentioned above, existing approaches generally fail to provide a high level of accuracy at a low cost. The present inventors have recognized, among other things, that stroke diagnosis can be done using a prehospital mobile telemedicine videoconference system, such as can assist to provide a high level of stroke diagnostic accuracy at a low cost.

In an example, a prehospital mobile telemedicine videoconference can be initiated between a device in a vehicle, such as an ambulance, carrying a patient suspected to have symptoms of a stroke and a device used by a clinician qualified to assess potential strokes, such as a neurologist. The device in the vehicle can use a camera to capture information about the patient, and the device used by the clinician can display the captured information. In an example, the device used by the clinician can receive input from the clinician including a determination indicating that the patient is exhibiting symptoms of a stroke. In response to obtaining input, the device used by the clinician can send the determination to the device in the vehicle. The device used by the clinician can generate a medical alert including patient information and the determination.

The prehospital mobile telemedicine videoconference can be used to diagnose or treat a patient, suspected to have symptoms of a stroke, while the patient is in an ambulance or other vehicle in transit to a hospital. In an example, the prehospital mobile telemedicine videoconference can support a diagnosis before a patient arrives at a hospital, allowing treatment to commence sooner than would be possible otherwise.

This overview is intended to provide an overview of subject matter of the present patent application. It is not intended to provide an exclusive or exhaustive explanation of the invention. The detailed description is included to provide further information about the present patent application.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Determining a diagnosis that fits with a patient's symptoms can be a time consuming process. Various techniques can be used to speed up the diagnosis process. In an example, the diagnosis process for a patient that has symptoms of a stroke can be aided by evaluating the patient in a vehicle that is en route to a hospital. A vehicle can include an ambulance, a car, an emergency transport vehicle, or the like. Use of the phrase "hospital" can generally refer to a medical facility that is capable of treating a patient, including an emergency department, a clinic, an office, or the like.

In an example, a patient with symptoms of a stroke can be evaluated using a prehospital mobile telemedicine videoconference. The term prehospital can include a state or period of time before a patient arrives at a hospital. For example, prehospital can refer to a duration or state where a patient first develops a symptom before calling for emergency help, a duration when a patient is waiting for emergency help, a duration during which a patient travels to a hospital, a patient in need of treatment but not yet admitted, or the like. Mobile telemedicine can include diagnosis or treatment of a patient using mobile technology. For example, mobile telemedicine can include a device-to-device connection using a cellular network. In an example, mobile telemedicine can include a mobile device on one end of a connection and a non-mobile device on the other end of the connection. Mobile telemedicine can include video, audio, or data-driven medical treatment, advice, or determinations. A prehospital mobile telemedicine videoconference can include any combination of the above examples, such as a mobile device that records video of a patient traveling to a hospital and sends the video live, or substantially live, to a second device.

Figure 1:
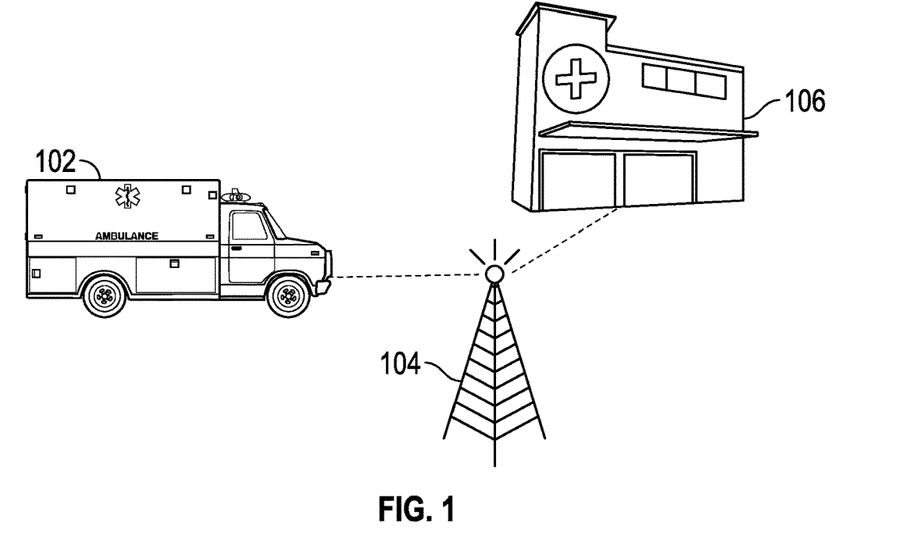
FIG. 1 illustrates generally an example of a communication system for a vehicle and a hospital.

FIG. 1 illustrates generally an example of a communication system for a vehicle 102 and a hospital 106 such as facilitated using a cellular tower 104 (e.g., a base station, Base Transceiver Station or an enhanced Node B). In an example, the vehicle 102, can transport a patient to the hospital 106. The vehicle 102 can be equipped with a mobile device capable of connecting to a device in the hospital 106 using the cell tower 104. For example, although only one cell tower 104 is shown in FIG. 1, one of ordinary skill in the art would understand that the mobile device can communicate with the device in the hospital 106 using multiple cell towers, multiple networks such as using a wide area network or trunk radio link, or the like. For example, the mobile device can connect to a hotspot or modem in the vehicle 102, and the hotspot can connect to the cell tower 104, such as an externally mounted antenna on the vehicle 102 to transmit high-speed mobile broadband data. A connection between the mobile device in the vehicle 102 and the device in the hospital 106, can be established, such that the mobile device and the device in the hospital 106 can establish a videoconference. For example, the mobile device in the vehicle 102 and the device in the hospital 106 can connect using a prehospital mobile telemedicine videoconference.

In an example, the prehospital mobile telemedicine videoconference can be a secure prehospital mobile telemedicine videoconference performed via a secure link in accordance with one or more health information encryption standards. The health information encryption standards can include industry standards, hospital standards, government standards such as those detailed in the Health Insurance Portability and Accountability Act (HIPAA), or the like.

A prehospital mobile telemedicine videoconference can be used to evaluate a patient for symptoms of a stroke. The patient can be in the vehicle 102, traveling to the hospital 106. In an example, it is useful to project an amount of time for the vehicle 102 transporting the patient to arrive at the hospital 106. Accurately assessing the symptoms of a stroke is not trivial and generally includes consultation with a specialist practitioner. According to various assessments, for example, the process can take about five to eight minutes to complete using a prehospital mobile telemedicine videoconference. Depending on the assessment used, other durations can be used, such as establishing a baseline of ten minutes, fifteen minutes, or other duration. Therefore, it can be useful to know the time the vehicle 102 transporting a patient will be in transit to the hospital 106, so that a comparison to the five to eight minute process time can be undertaken to determine if sufficient transit time exists to justify initiating a telemedicine session. For example, the five to eight minute process time can be considered a threshold and can act as a minimum amount of time required for a prehospital mobile telemedicine videoconference to evaluate a patient with symptoms of a stroke. A higher or lower threshold can be used depending on the methods used to evaluate the patient for symptoms of a stroke. If the patient has other symptoms not indicative of a stroke, other thresholds can be used. The threshold can be higher than the five to eight minute process time, such as ten or fifteen minutes, if additional information is needed using the prehospital mobile telemedicine videoconference.

In an example, the amount of time for the vehicle 102 transporting the patient to arrive at the hospital 106 can be projected using location identification, such as supported by global positioning satellites (GPS) or other techniques, such as to determine one or more of a position or velocity of the vehicle 102. The position of the hospital 106 can be determined using GPS or can be identified from a map, previous position determination, or the like. The position of the vehicle 102 relative to the hospital 106 can be determined. For example, a distance can be calculated using a route over roads that the vehicle 102 will travel to the hospital 106. An estimated speed can also be determined for the vehicle 102, such as by computing an average estimated speed, compiling speed limit data, identifying previously known speeds on the roads to be traveled by the vehicle 102, or the like, or a combination of any of the above. Using the distance or position of the vehicle 102 relative to the hospital 106 and the estimated speed of the vehicle 102, an amount of time for the vehicle 102 transporting the patient to arrive at the hospital 106 can be projected. In an example, a dispatch device, such as a device in communication with the vehicle 102, but not located in the vehicle 102, can project the amount of time. In another example, a device in the vehicle 102 can project the amount of time. Similarly, a device in the hospital 106 can project the amount of time. Once the projected amount of time is known, it can be compared to the threshold to determine if the vehicle 102 will take longer than the threshold to arrive at the hospital 106. If the projected amount of time is greater than the threshold, a prehospital mobile telemedicine videoconference can be initiated to evaluate a patient with symptoms of a stroke in the vehicle 102 while traveling to the hospital 106.

Figure 2:
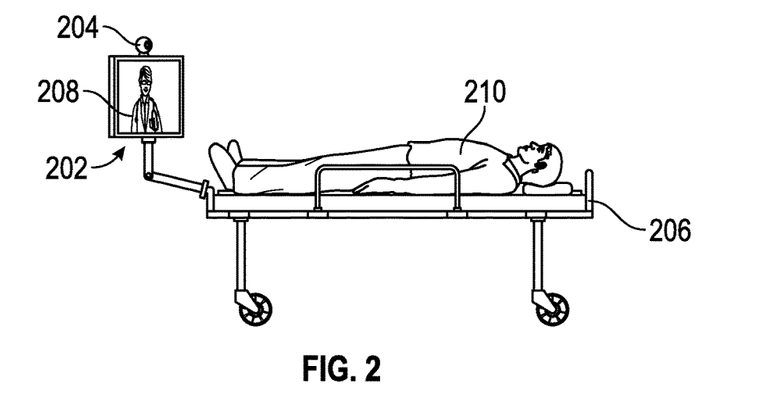
FIG. 2 illustrates generally an illustrative example of a vehicle-based communication system in a prehospital mobile telemedicine videoconference system.

FIG. 2 illustrates generally an illustrative example of a vehicle-based communication system in a prehospital mobile telemedicine videoconference system. FIG. 2 shows an ambulance device 202, also known as a vehicle device, with a patient camera 204. In FIG. 2, an example of a setup is shown in which the ambulance device 202 is mechanically coupled to a stretcher 206. The stretcher 206 can be any support structure that a patient 210 occupies in a vehicle, such as a chair, a bench, a bed, a traditional stretcher, or the like. In another example, the ambulance device 202 can be mechanically coupled to a vehicle carrying a patient. The ambulance device 202 can also be a handheld device, supported by an emergency medical technician (EMT) in a vehicle. In an example, the ambulance device 202 shows a doctor 208, such as any person qualified to evaluate the patient 210 for symptoms of a stroke (e.g., a physician, a neurologist, etc.). The patient camera 204 can be arranged such that it can capture the patient 210. The ambulance device 202 can be arranged such that it can be viewed by a person in the vehicle, such as the EMT or the patient 210, while displaying the doctor 208. In an example, the ambulance device 202 can include a tablet device, such as an Apple® iPad, or the like, a cellular telephone, a laptop, or the like. In an example, the ambulance device 202 can initiate or receive a prehospital mobile telemedicine videoconference request with another device.

Figure 3:
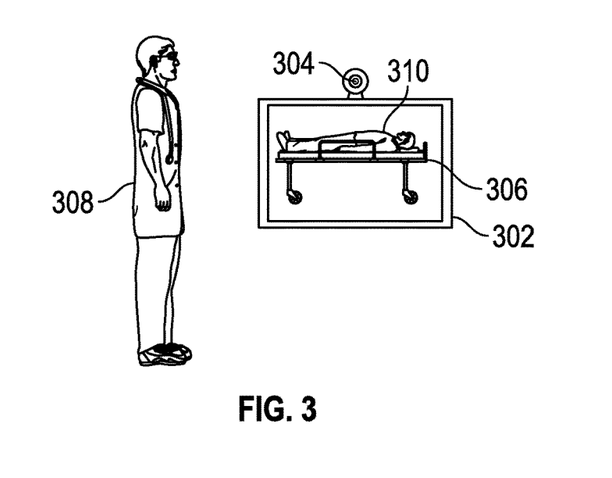
FIG. 3 illustrates generally an illustrative example of an evaluation system in a prehospital mobile telemedicine videoconference system.

FIG. 3 illustrates generally an illustrative example of an evaluation system in a prehospital mobile telemedicine videoconference system. FIG. 3 shows a doctor device 302, with a doctor camera 304. In an example, the doctor device 302 can include a tablet device, such as an Apple® iPad, or the like, a cellular telephone, a laptop, or the like. In an example, the doctor device 302 can initiate or receive a prehospital mobile telemedicine videoconference request with another device. The doctor device 302 can be used by any clinician qualified to evaluate a patient 310 for symptoms of a stroke, such as a physician, a neurologist, etc. The doctor device 302 can be configured to show the patient 310 on a display. The doctor device 302 can be configured to allow a clinician qualified to evaluate the patient 310 for symptoms of a stroke, such as a doctor 308 to do such an evaluation. The doctor camera 304 can be configured to capture the doctor 308 and display the doctor 308 on a remote device, such as the ambulance device 202 shown in FIG. 2. In an example, the doctor device 302 can be a mobile device, such as those described above, or a non-mobile device, such as a television, a desktop computer, or the like. A prehospital mobile telemedicine videoconference can use one or more mobile devices, but does not require that all devices be mobile. The doctor device 302 can display a stretcher 306, which can be any of the apparatuses described above with respect to the stretcher 206 of FIG. 2. The doctor device 302 can also display an EMT who is proximate to the patient 310, such as an EMT in a vehicle with the patient 310. Using a prehospital mobile telemedicine videoconference over the doctor device 302 in communication with a device such as the ambulance device 202 of FIG. 2, the doctor 308 can evaluate the patient 310 for symptoms of a stroke.

In an example, symptoms of a stroke in a patient can be determined using various medical techniques known in the art. One such technique involves administering an 11 step assessment published by the National Institutes of Health (NIH) called the NIH Stroke Scale (NIHSS). An example of the assessment can be found at http://www.ninds.nih.gov/doctors/NIH_Stroke_Scale.pdf and is herein incorporated by reference in its entirety. For example, a clinician qualified to evaluate a patient for symptoms of a stroke can use the assessment or another stroke evaluation technique to determine if a patient is exhibiting symptoms of a stroke. These techniques can be completed using a prehospital mobile telemedicine videoconference when a patient is traveling to a hospital. Other evaluations can be done before or after the techniques, such as determining patient histories, identifying allergies, or the like. In an example, a technique for evaluating a patient for symptoms of a stroke can include determining a patient's level of consciousness, asking the patient questions, instructing the patient to complete a series of tasks, evaluating physical traits of the patient, or the like. In an example, evaluating a patient for symptoms of a stroke using a prehospital mobile telemedicine videoconference can occur after a dispatcher or an EMT determines that the patient might have symptoms of a stroke. The dispatcher or the EMT can determine that the patient might have symptoms of a stroke using any of the above identified techniques, abbreviated versions of those techniques, other assessments, or the like. For example, a dispatcher can use information obtained by talking to a patient on a telephone to determine that the patient might have symptoms of a stroke. The dispatcher can then send an ambulance to pick up the patient. An EMT in the ambulance can evaluate the patient while the ambulance is transporting the patient to a hospital. The EMT evaluating the patient can use any of the above techniques to determine that the patient has or might have symptoms of a stroke. A prehospital mobile telemedicine conference can be initiated after the patient is picked up by the ambulance, and the initiation can occur before or after the EMT evaluates the patient.

Figure 4:
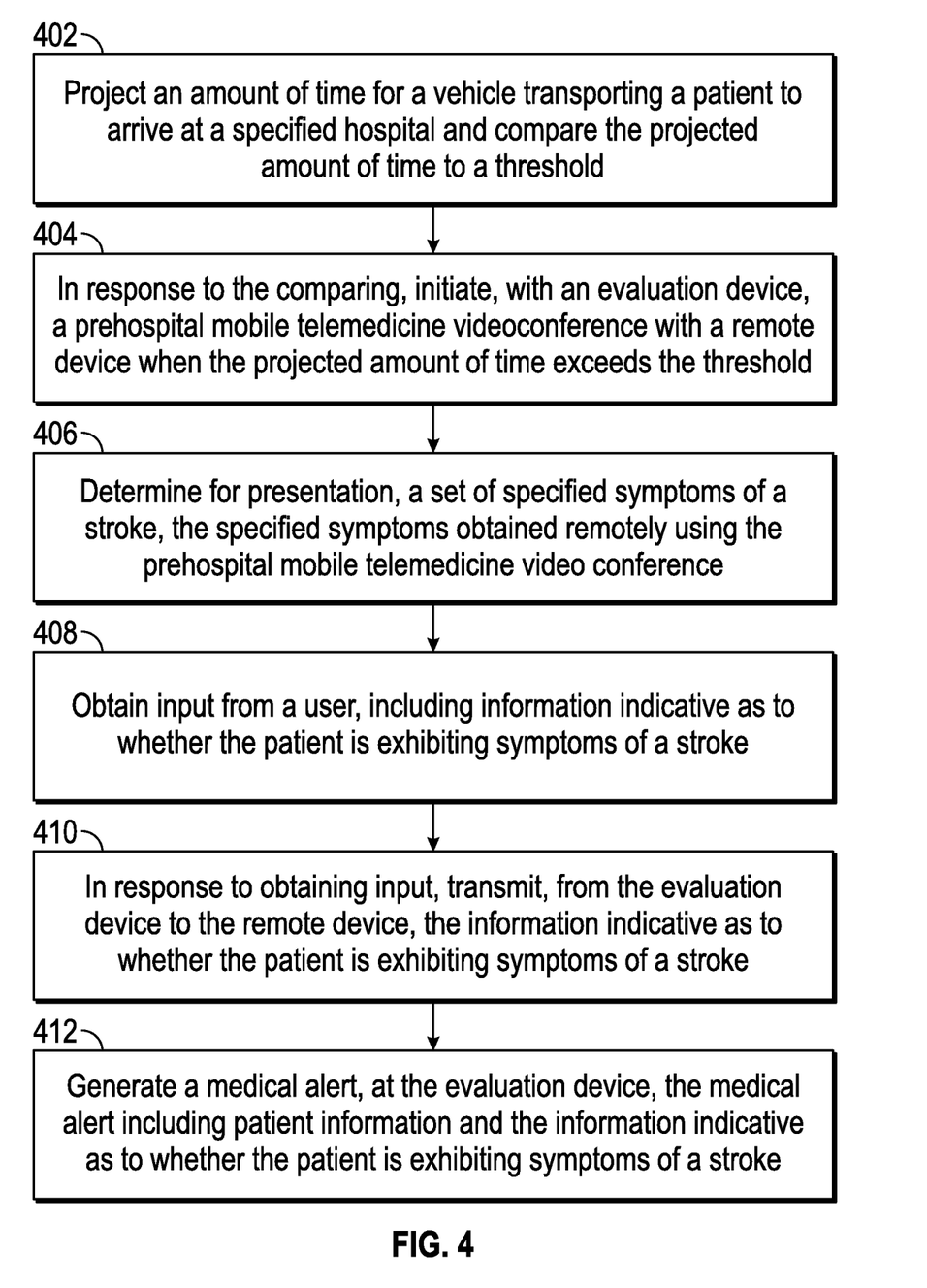
FIG. 4 illustrates generally a technique, such as a method, that can include evaluating a patient using a prehospital mobile telemedicine videoconference.

FIG. 4 illustrates generally a technique, such as a method, that can include projecting an amount of time for a vehicle transporting a patient to arrive at a specified hospital and comparing the projected amount of time to a threshold 402 and in response to the comparing, initiating, with an evaluation device, a prehospital mobile telemedicine videoconference with a remote device when the projected amount of time exceeds the threshold 404. The technique can include receiving, for presentation during the prehospital mobile telemedicine videoconference, physiologic information, where at least some of the physiologic information is obtained from the patient during transport, or the technique can include determining for presentation, a set of specified symptoms of a stroke, the specified symptoms obtained remotely using the prehospital mobile telemedicine videoconference 406. The technique can include obtaining input from a user, including information indicative as to whether the patient is exhibiting symptoms of a stroke 408, and in response to obtaining input, transmitting from the evaluation device to the remote device, the information indicative as to whether the patient is exhibiting symptoms of a stroke 410. The technique can include generating a medical alert, at the evaluation device, the medical alert including patient information and the information indicative as to whether the patient is exhibiting symptoms of a stroke 412.

In an example, physiologic information can include video, audio, or other data, such as patient vital signs. For example, patient vital signs can include blood pressure, pulse or heart rate information, pupil dilation or response, temperature, affect or the like. Audio can include patient speech, ambient noise, EMT speech, or the like. Similarly, video can include a series of images of a patient, an EMT, or the like.

In an example, the medical alert of FIG. 4 can include information indicative that the patient is exhibiting symptoms of a stroke. For example, the medical alert can be sent to the specified hospital such that the specified hospital receives a notification that the patient will arrive in a specified amount of time and that the patient's symptoms include symptoms of a stroke.

In an example, the medical alert of FIG. 4 can include information indicative that the patient is not exhibiting symptoms of a stroke. For example, if the patient is not exhibiting symptoms of a stroke, the vehicle can be rerouted to a hospital different from the specified hospital. The vehicle can also continue to the specified hospital. The medical alert can alert whatever hospital to which the vehicle takes the patient that the patient will arrive in a specified amount of time. The medical alert can indicate the patient's symptoms and indicate that the patient's symptoms are not symptoms of a stroke.

In an example, the specified hospital of FIG. 4 can include an x-ray computed tomography (CT) scanner, which can be referred to as a CAT Scan, a CAT scanner, or the like. For example, the CT scanner can be located proximately to the door where the vehicle of FIG. 4 will arrive at the specified hospital with the patient. The specified hospital can include a device for receiving the medical alert.

In an example, the patient of FIG. 4 can be treated at the hospital for a stroke if the medical alert includes information indicative that the patient is exhibiting symptoms of a stroke. For example, a CT scan of the patient can be taken. The CT scan can confirm that the patient has had a stroke and can further indicate whether the stroke was an ischemic stroke or a hemorrhagic stroke. In an example, if the patient suffered from an ischemic stroke, the patient can be given a thrombolytic agent, such as a tissue plasminogen activator (tPA), to treat the ischemic stroke.

In an example, the medical alert of FIG. 4 can be sent to the specified hospital, a different hospital, the doctor device 302 of FIG. 3, a dispatch device, or the like, or any combination of the above. The medical alert can include patient information such as a patient history, allergies, medical information, or the like. The medical alert can include an electronic medical record for the patient, which can include all or part of the patient information. The medical alert can be sent to a database for storing all or part of the medical alert, such as storing the electronic medical record for the patient.

In an example, the above detailed systems and techniques can be used to facilitate prehospital emergency medical research, such as by using a prehospital mobile telemedicine videoconference. The prehospital emergency medical research can include evaluating a patient for symptoms, conducting research on reliability of prehospital mobile telemedicine videoconferences, or the like. For example, an investigator can communicate with a patient during transport in an ambulance using a prehospital mobile telemedicine videoconference. The patient can then be evaluated after arrival at a hospital and the results of the communication and the evaluation can be compared to determine effectiveness of the communication.

Figure 5:
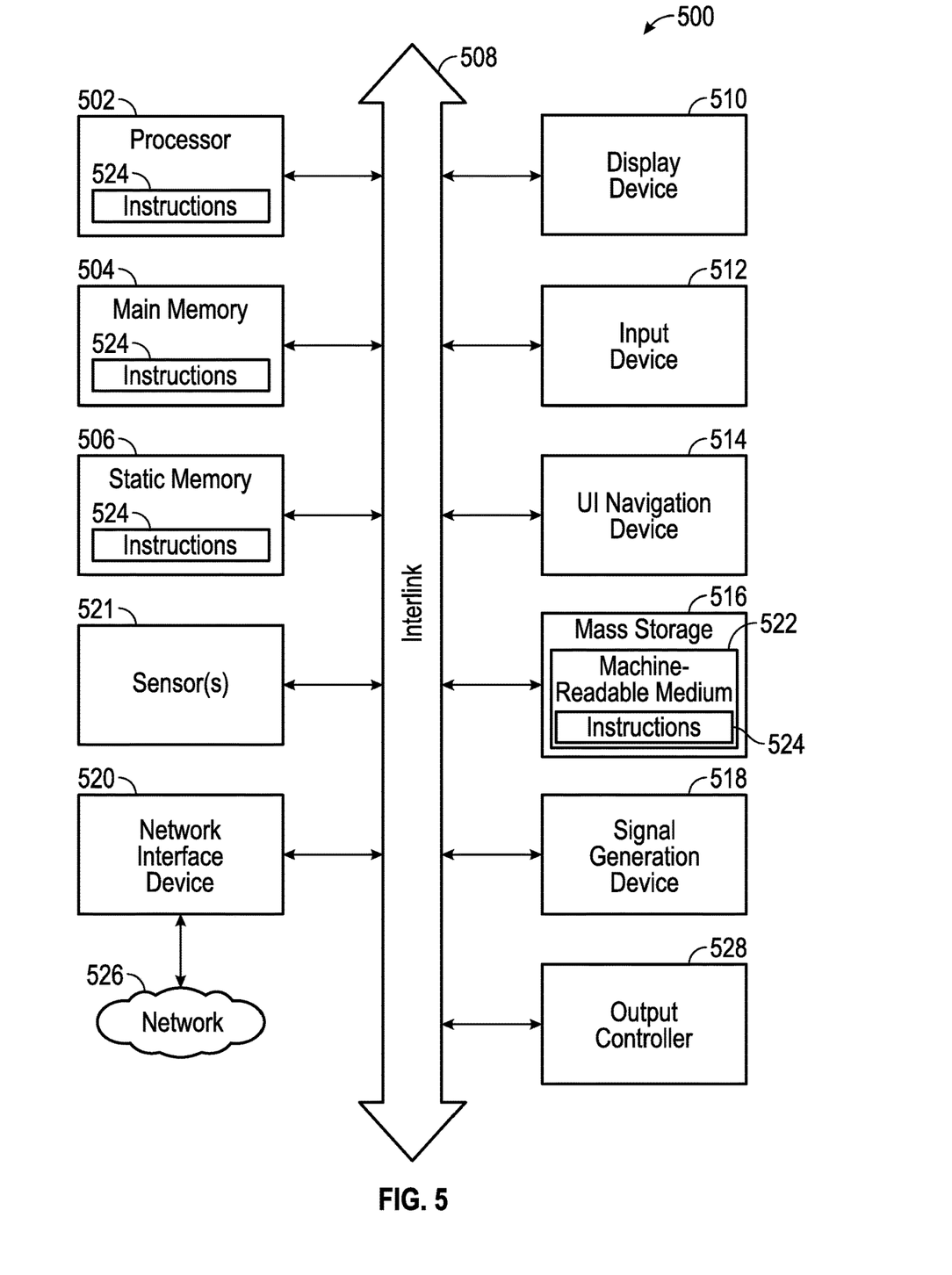
FIG. 5 illustrates generally an illustrative example of a block diagram of a machine upon which one or more embodiments can be implemented.

FIG. 5 illustrates generally an example of a block diagram of a machine 500 upon which any one or more of the techniques (e.g., methodologies) discussed herein can perform in accordance with some embodiments. In alternative embodiments, the machine 500 can operate as a standalone device or can be connected (e.g., networked) to other machines. In a networked deployment, the machine 500 can operate in the capacity of a server machine, a client machine, or both in server-client network environments. In an example, the machine 500 can act as a peer machine in peer-to-peer (P2P) (or other distributed) network environment. The machine 500 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, can include, or can operate on, logic or a number of components, modules, or mechanisms. Modules are tangible entities (e.g., hardware) capable of performing specified operations when operating. A module includes hardware. In an example, the hardware can be specifically configured to carry out a specific operation (e.g., hardwired). In an example, the hardware can include configurable execution units (e.g., transistors, circuits, etc.) and a computer readable medium containing instructions, where the instructions configure the execution units to carry out a specific operation when in operation. The configuring can occur under the direction of the executions units or a loading mechanism. Accordingly, the execution units are communicatively coupled to the computer readable medium when the device is operating. In this example, the execution units can be a member of more than one module. For example, under operation, the execution units can be configured by a first set of instructions to implement a first module at one point in time and reconfigured by a second set of instructions to implement a second module.

Machine (e.g., a computer system) 500 can include a hardware processor 502 (e.g., a central processing unit (CPU), a graphics processing unit (GPU), a hardware processor core, or any combination thereof), a main memory 504 and a static memory 506, some or all of which can communicate with each other via an interlink (e.g., bus) 508. The machine 500 can further include a display unit 510, an alphanumeric input device 512 (e.g., a keyboard), and a user interface (UI) navigation device 514 (e.g., a mouse). In an example, the display unit 510, alphanumeric input device 512 and UI navigation device 514 can be a touch screen display. The machine 500 can additionally include a storage device (e.g., drive unit) 516, a signal generation device 518 (e.g., a speaker), a network interface device 520, and one or more sensors 521, such as a global positioning system (GPS) sensor, compass, accelerometer, or other sensor. The machine 500 can include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 516 can include a machine readable medium 522 that is non-transitory on which is stored one or more sets of data structures or instructions 524 (e.g., software) embodying or utilized by any one or more of the techniques or functions described herein. The instructions 524 can also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 can constitute machine readable media.

While the machine readable medium 522 is illustrated as a single medium, the term "machine readable medium" can include a single medium or multiple media (e.g., a centralized or distributed database, or associated caches and servers) configured to store the one or more instructions 524.

The term "machine readable medium" can include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine readable medium examples can include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 524 can further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 520 can include one or more physical jacks (e.g., Ethernet, coaxial, or phone jacks) or one or more antennas to connect to the communications network 526. In an example, the network interface device 520 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 500, and includes digital or analog communications signals or other intangible medium to facilitate communication of such software.

VARIOUS NOTES & EXAMPLES

Example 1 includes the subject matter embodied by a method for facilitating mobile telemedicine for a suspected stroke case comprising: projecting an amount of time, for a vehicle transporting a patient, to arrive at a specified hospital, comparing the projected amount of time to a threshold, in response to the comparing, initiating, with an evaluation device, a prehospital mobile telemedicine videoconference with a remote device when the projected amount of time exceeds the threshold, receiving, for presentation during the prehospital mobile telemedicine videoconference, physiologic information, where at least some of the physiologic information is obtained from the patient during transport, obtaining input from a user, including information indicative as to whether the patient is exhibiting symptoms of a stroke, in response to obtaining input, transmitting, from the evaluation device to the remote device, the information indicative as to whether the patient is exhibiting symptoms of a stroke, and generating a medical alert, at the evaluation device, the medical alert including patient information and the information indicative as to whether the patient is exhibiting symptoms of a stroke.

In Example 2, the subject matter of Example 1 can optionally include wherein the information indicative as to whether the patient is exhibiting symptoms of a stroke includes information indicative that the patient is exhibiting symptoms of a stroke.

In Example 3, the subject matter of one or any combination of Examples 1-2 can optionally include wherein in response to the information indicative that the patient is exhibiting symptoms of a stroke, transmitting the medical alert from the evaluation device to the remote device, wherein the medical alert further comprises instructions to proceed to the specified hospital.

In Example 4, the subject matter of one or any combination of Examples 1-3 can optionally include wherein the information indicative as to whether the patient is exhibiting symptoms of a stroke includes information indicative that the patient is not exhibiting symptoms of a stroke.

In Example 5, the subject matter of one or any combination of Examples 1-4 can optionally include wherein in response to the information indicative that the patient is not exhibiting symptoms of a stroke, transmitting the medical alert from the evaluation device to the remote device, wherein the medical alert further comprises instructions to proceed to a second hospital different from the specified hospital.

In Example 6, the subject matter of one or any combination of Examples 1-5 can optionally include transmitting the medical alert from the evaluation device to a medical information system.

In Example 7, the subject matter of one or any combination of Examples 1-6 can optionally include wherein the vehicle is an ambulance.

In Example 8, the subject matter of one or any combination of Examples 1-7 can optionally include wherein projecting an amount of time includes projecting, at the evaluation device, using a current location of the ambulance, a location of the hospital, and a specified ambulance speed.

In Example 9, the subject matter of one or any combination of Examples 1-8 can optionally include wherein the threshold is 10 minutes.

In Example 10, the subject matter of one or any combination of Examples 1-9 can optionally include wherein the prehospital mobile telemedicine videoconference is a secure prehospital mobile telemedicine videoconference performed via a secure link in accordance with one or more health information encryption standards.

In Example 11, the subject matter of one or any combination of Examples 1-10 can optionally include wherein the patient information comprises an electronic medical record for the patient.

In Example 12, the subject matter of one or any combination of Examples 1-11 can optionally include wherein the remote device is a mobile device mechanically coupled to the ambulance or the remote device is a mobile device mechanically coupled to a stretcher holding the patient.

In Example 13, the subject matter of one or any combination of Examples 1-12 can optionally include wherein the medical alert includes instructions to prepare a (computed tomography) CT scanner for the patient.

In Example 14, the subject matter of one or any combination of Examples 1-13 can optionally include wherein the medical alert includes instructions to use the CT scanner to determine that the patient exhibits the set of specified symptoms of an ischemic stroke.

In Example 15, the subject matter of one or any combination of Examples 1-14 can optionally include wherein the medical alert includes instructions, in response to determining that the patient exhibits the set of specified symptoms of an ischemic stroke, to administer a thrombolytic agent to the patient.

In Example 16, the subject matter of one or any combination of Examples 1-15 can optionally include wherein the evaluation device is a mobile computing device.

Example 17 can include, or can optionally be combined with all of portions of the subject matter of one or any combination of Examples 1-(XX-1) to include the subject matter embodied by a method for facilitating mobile telemedicine for a suspected stroke case comprising: projecting an amount of time, for a vehicle transporting a patient, to arrive at a specified hospital, comparing the projected amount of time to a threshold, in response to the comparing, initiating, with a mobile computing device, a prehospital mobile telemedicine videoconference with an evaluation device when the projected amount of time exceeds the threshold, receiving, at the mobile computing device from the evaluation device, a determined set of specified symptoms of a stroke and information indicative as to whether the patient is exhibiting symptoms of a stroke, using the prehospital mobile telemedicine videoconference, and generating a medical alert, at the mobile computing device, the medical alert including patient information and the information indicative as to whether the patient is exhibiting symptoms of a stroke.

In Example 18, the subject matter of Example 17 can optionally include wherein before receiving the determined set of specified symptoms of a stroke, sending, from the mobile computing device to the evaluation device, a projected set of specified symptoms of a stroke.

Example 19 can include, or can optionally be combined with all of portions of the subject matter of one or any combination of Examples 1-(XX-1) to include the subject matter embodied by a system for facilitating mobile telemedicine for a suspected stroke case comprising: a scheduling module to: project an amount of time for a vehicle transporting a patient to arrive at a specified hospital, compare the projected amount of time to a threshold, and send the comparison to a communication module, the communication module to: in response to the comparison, initiate a prehospital mobile telemedicine videoconference with a remote device when the projected amount of time exceeds the threshold, an evaluation module to: receive, for presentation during the prehospital mobile telemedicine videoconference, physiologic information, where at least some of the physiologic information is obtained from the patient during transport, and obtain input from a user, including information indicative as to whether the patient is exhibiting symptoms of a stroke, and the communication module to: in response to obtaining input, transmit to the remote device the information indicative as to whether the patient is exhibiting symptoms of a stroke, and generate a medical alert, the medical alert including patient information and the information indicative as to whether the patient is exhibiting symptoms of a stroke.

In Example 20, the subject matter of Example 19 can optionally include wherein the information indicative as to whether the patient is exhibiting symptoms of a stroke includes information indicative that the patient is exhibiting symptoms of a stroke, and wherein the communication module is further configured to transmit the medical alert to the remote device, wherein the medical alert further comprises instructions to proceed to the specified hospital.

In Example 21, the subject matter of one or any combination of Examples 19-20 can optionally include wherein the communication module is further configured to transmit the medical alert to a medical information system.

In Example 22, the subject matter of one or any combination of Examples 19-21 can optionally include wherein to project the amount of time, the scheduling module is further configured to project the amount of time using a current location of the ambulance, a location of the hospital, and an specified ambulance speed.

In Example 23, the subject matter of one or any combination of Examples 19-22 can optionally include wherein the remote device is a mobile device mechanically coupled to the ambulance or the remote device is a mobile device mechanically coupled to a stretcher holding the patient.

In Example 24, the subject matter of one or any combination of Examples 19-23 can optionally include wherein the medical alert includes instructions to prepare a CT scanner for the patient.

Example 25 can include, or can optionally be combined with all of portions of the subject matter of one or any combination of Examples 1-24 to include the subject matter embodied by a system for facilitating mobile telemedicine for a suspected stroke case comprising: a scheduling module to: project an amount of time for a vehicle transporting a patient to arrive at a specified hospital, compare the projected amount of time to a threshold, and send the comparison to a communication module, and a communication module to: in response to the comparison, initiating, with a mobile computing device, a prehospital telemedicine videoconference with an evaluation device when the projected amount of time exceeds the threshold, receive, from the evaluation device, a set of specified symptoms of a stroke and information indicative as to whether the patient is exhibiting symptoms of a stroke, using the prehospital mobile telemedicine videoconference, and generate a medical alert, the medical alert including patient information and the information indicative as to whether the patient is exhibiting symptoms of a stroke.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What I claim is:

1. A system for facilitating mobile telemedicine for a suspected stroke case comprising:
a processor of a mobile device;
memory of the mobile device, the memory coupled to the processor, the memory including instructions, which when executed by the processor, cause the processor to:
project an amount of time for a vehicle transporting a patient to arrive at a specified hospital;
select an evaluation threshold based on patient treatment parameters;
compare the projected amount of time to the evaluation threshold, the evaluation threshold indicating a minimum amount of time required for a prehospital telemedicine videoconference; and
in response to the comparison, initiate, with a mobile computing device, the prehospital telemedicine videoconference with an evaluation device when the projected amount of time exceeds the evaluation threshold;
receive, from the evaluation device, a set of specified symptoms of a stroke and information indicative as to whether the patient is exhibiting symptoms of a stroke, using the prehospital mobile telemedicine videoconference; and
generate a medical alert, the medical alert including patient information and the information indicative as to whether the patient is exhibiting symptoms of a stroke.

2. A method for facilitating mobile telemedicine for a suspected stroke case comprising:
projecting, via a processor of a mobile device, an amount of time, for a vehicle transporting a patient, to arrive at a specified hospital;
selecting an evaluation threshold based on patient treatment parameters;
comparing the projected amount of time to the evaluation threshold, the evaluation threshold indicating a minimum amount of time required for a prehospital telemedicine videoconference;
in response to the comparing, initiating, with an evaluation device, the prehospital mobile telemedicine videoconference with a remote device when the projected amount of time exceeds the evaluation threshold;
receiving, for presentation during the prehospital mobile telemedicine videoconference, physiologic information, where at least some of the physiologic information is obtained from the patient during transport;
obtaining input from a user, including information indicative as to whether the patient is exhibiting symptoms of a stroke;
in response to obtaining input, transmitting, from the evaluation device to the remote device, the information indicative as to whether the patient is exhibiting symptoms of a stroke; and
generating a medical alert, at the evaluation device, the medical alert including patient information and the information indicative as to whether the patient is exhibiting symptoms of a stroke.

3. The method of claim 2, wherein the information indicative as to whether the patient is exhibiting symptoms of a stroke includes information indicative that the patient is exhibiting symptoms of a stroke.

4. The method of claim 3, wherein in response to the information indicative that the patient is exhibiting symptoms of a stroke, transmitting the medical alert from the evaluation device to the remote device, wherein the medical alert further comprises instructions to proceed to the specified hospital.

5. The method of claim 2, wherein the information indicative as to whether the patient is exhibiting symptoms of a stroke includes information indicative that the patient is not exhibiting symptoms of a stroke.

6. The method of claim 5, wherein in response to the information indicative that the patient is not exhibiting symptoms of a stroke, transmitting the medical alert from the evaluation device to the remote device, wherein the medical alert further comprises instructions to proceed to a second hospital different from the specified hospital.

7. The method of claim 2, further comprising, transmitting the medical alert from the evaluation device to a medical information system.

8. The method of claim 2, wherein the vehicle is an ambulance.

9. The method of claim 2, wherein projecting an amount of time includes projecting, at the evaluation device, using a current location of the ambulance, a location of the hospital, and a specified ambulance speed.

10. The method of claim 2, wherein the evaluation threshold is 10 minutes.

11. The method of claim 2, wherein the prehospital mobile telemedicine videoconference is a secure prehospital mobile telemedicine videoconference performed via a secure link in accordance with one or more health information encryption standards.

12. The method of claim 2, wherein the patient information comprises an electronic medical record for the patient.

13. The method of claim 2, wherein the remote device is a mobile device mechanically coupled to the ambulance or the remote device is a mobile device mechanically coupled to a stretcher holding the patient.

14. The method of claim 2, wherein the medical alert includes instructions to prepare a computed tomography (CT) scanner for the patient.

15. The method of claim 14, wherein the medical alert includes instructions to use the CT scanner to determine that the patient exhibits the set of specified symptoms of an ischemic stroke.

16. The method of claim 15, wherein the medical alert includes instructions, in response to determining that the patient exhibits the set of specified symptoms of an ischemic stroke, to administer a thrombolytic agent to the patient.

17. The method of claim 16, wherein the evaluation device is a mobile computing device.

18. A method for facilitating mobile telemedicine for a suspected stroke case comprising:
- projecting, via a processor of a mobile device, an amount of time, for a vehicle transporting a patient, to arrive at a specified hospital;
- selecting an evaluation threshold based on patient treatment parameters;
- comparing the projected amount of time to the evaluation threshold, the evaluation threshold indicating a minimum amount of time required for a prehospital telemedicine videoconference;
- in response to the comparing, initiating, with a mobile computing device, a prehospital mobile telemedicine videoconference with an evaluation device when the projected amount of time exceeds the evaluation threshold;
- receiving, at the mobile computing device from the evaluation device, a determined set of specified symptoms of a stroke and information indicative as to whether the patient is exhibiting symptoms of a stroke, using the prehospital mobile telemedicine videoconference; and
- generating a medical alert, at the mobile computing device, the medical alert including patient information and the information indicative as to whether the patient is exhibiting symptoms of a stroke.

19. The method of claim 18, wherein before receiving the determined set of specified symptoms of a stroke, sending, from the mobile computing device to the evaluation device, a projected set of specified symptoms of a stroke.

20. A system for facilitating mobile telemedicine for a suspected stroke case comprising:
- a processor of a mobile device;
- memory of the mobile device, the memory coupled to the processor, the memory including instructions, which when executed by the processor, cause the processor to:
- project an amount of time for a vehicle transporting a patient to arrive at a specified hospital;
- select an evaluation threshold based on patient treatment parameters;
- compare the projected amount of time to the evaluation threshold, the evaluation threshold indicating a minimum amount of time required for a prehospital telemedicine videoconference; and
- in response to the comparison, initiate a prehospital mobile telemedicine videoconference with a remote device when the projected amount of time exceeds the evaluation threshold;
- receive, for presentation during the prehospital mobile telemedicine videoconference, physiologic information, where at least some of the physiologic information is obtained from the patient during transport; and
- obtain input from a user, including information indicative as to whether the patient is exhibiting symptoms of a stroke; and
- in response to obtaining input, transmit to the remote device the information indicative as to whether the patient is exhibiting symptoms of a stroke; and
- generate a medical alert, the medical alert including patient information and the information indicative as to whether the patient is exhibiting symptoms of a stroke.

21. The system of claim 20, wherein the information indicative as to whether the patient is exhibiting symptoms of a stroke includes information indicative that the patient is exhibiting symptoms of a stroke; and
- wherein the processor is further configured to transmit the medical alert to the remote device, wherein the medical alert further comprises instructions to proceed to the specified hospital.

22. The system of claim 20, wherein the processor is further configured to transmit the medical alert to a medical information system.

23. The system of claim 20, wherein to project the amount of time, the processor is further configured to project the amount of time using a current location of the ambulance, a location of the hospital, and a specified ambulance speed.

24. The system of claim 20, wherein the remote device is a mobile device mechanically coupled to the ambulance or the remote device is a mobile device mechanically coupled to a stretcher holding the patient.

25. The system of claim 24, wherein the medical alert includes instructions to prepare a computed tomography (CT) scanner for the patient.

* * * * *